United States Patent [19]

Tamai et al.

[11] Patent Number: 5,385,935
[45] Date of Patent: Jan. 31, 1995

[54] METHOD FOR THE INHIBITION OF RESTENOSIS ASSOCIATED WITH CORONARY INTERVENTION

[75] Inventors: Hideo Tamai, Moriyama; Kinzo Ueda, Kusatsu; Yung-sheng Hsu, Moriyama, all of Japan

[73] Assignee: Kissei Pharmaceutical Co., Ltd., Japan

[21] Appl. No.: 116,701

[22] Filed: Sep. 7, 1993

[30] Foreign Application Priority Data

Sep. 14, 1992 [JP] Japan ................................ 4-288086

[51] Int. Cl.⁶ ............................................ A61K 31/24
[52] U.S. Cl. .................................... 514/535; 514/930
[58] Field of Search ...................... 514/535, 563, 930; 549/441

[56] References Cited

U.S. PATENT DOCUMENTS

| | | | |
|---|---|---|---|
| 3,940,422 | 2/1976 | Harita et al. | 549/441 |
| 4,070,484 | 1/1978 | Harita et al. | 514/535 |
| 4,337,270 | 6/1982 | Noda et al. | 514/535 |

OTHER PUBLICATIONS

Garcia, Mesa, "New approach to the mechanism of antiasthmatic action of Tranilast" *Allergol Immunopathol*, vol. 18 issue (1). 1990.

*Primary Examiner*—Raymond J. Henley, III
*Assistant Examiner*—K. Weddington
*Attorney, Agent, or Firm*—DePaoli & Frenkel

[57] ABSTRACT

This invention provides a method for treating patients to inhibit restenosis associated with coronary intervention. A 600 mg dosage of Tranilast for a treatment period of three consecutive months after coronary intervention lowers the incidence of restenosis, and reduces the degree of stenosis in patients.

8 Claims, No Drawings

METHOD FOR THE INHIBITION OF RESTENOSIS ASSOCIATED WITH CORONARY INTERVENTION

FIELD OF THE INVENTION The present invention relates to a method for the inhibition of restenosis associated with coronary intervention.

More particularly, the method comprises administrating to a human patient after coronary intervention an oral or parenteral dose of 2-(2,3-dimethoxycinnamoyl-)aminobenzoic acid (Tranilast) represented by the following formula (I) or a pharmaceutically acceptable salt thereof as an active ingredient.

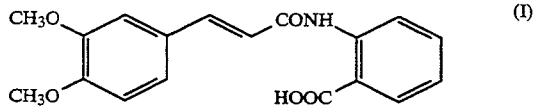

Illustrative of pharmaceutically acceptable salts are inorganic salts such as sodium or calcium salt, or organic salts formed with amines such as morpholine, piperidine, arginine, and the like.

As coronary intervention in the present invention, for example, Percutaneous Transluminal Coronary Angioplasty (PTCA), Direction Coronary Atherectomy and Stent can be included.

BACKGROUND OF THE INVENTION

1. Technical Field of the Invention

Coronary intervention is a surgical approach to the treatment of ischemic heart diseases such as angina pectoris and myocardial infarction. Coronary intervention technically involves mechanical revascularization of a stenosed lesion in a coronary artery by means of a balloon catheter, an atherectomy catheter and the like. As a consequence, coronary intervention often causes restenosis due to damaged intima cells.

Up to the present time, there has not been any effective drug for the treatment or prevention of restenosis associated with coronary intervention.

2. DESCRIPTION OF THE RELATED ART

Tranilast is sold commercially as a drug for the treatment of allergic diseases, e.g., allergic bronchitis, allergic asthma, atopic dermatitis, and the like, based on the activity exhibited by the drug for inhibiting release of chemical mediators [The Journal of Allergy and Clinical Immunology, Vol. 57, No. 5, pp. 396-407, (1976)].

Recently, in Biochemical Pharmacology, Vol.36, No. 4, pp. 469-474 (1987), it was reported that Tranilast inhibits fibroblast proliferation and collagen accumulation.

Further, it is noted of record that the authors of the present invention embodiments reported in Japanese College of Cardiology (1988) the treatment of patients subjected to PTCA surgery with Tranilast in a daily oral dose of 300 mg for 30 consecutive days after the PTCA surgery. The clinical data did not indicate any significant efficacy for preventing a restenosis effect associated with PTCA surgery.

SUMMARY OF THE INVENTION

An object of the present invention is to provide a method for the prevention or treatment of restenosis associated with coronary intervention by administering 2-(3,4-dimethoxycinnamoyl)aminobenzoic acid or pharmaceutically acceptable salt thereof to an adult patient after coronary intervention.

Other objects, features and advantages of the present invention will become apparent from the following description and examples.

DETAILED DESCRIPTION OF THE INVENTION

It is documented that restenosis associated with coronary intervention occurs within a period of about six months after coronary intervention. The clinical test data described in the Description Of The Related Art above were obtained over a test period of 30 consecutive days after the PTCA surgery. It was speculated by the present inventors that the lack of any significant efficacy for preventing a restenosis effect with Tranilast might be due to the relatively short 30 day duration of the drug treatment after PTCA surgery.

Further clinical testing of patients was conducted to determine if an extended period of Tranilast treatment might be effective for lowering the incidence of post-surgery restenosis associated with PTCA. It was found that Tranilast dosage of patients for a duration of at least about three months (i.e., a term of at least about 90 consecutive days of treatment) reduced the incidence of restenosis associated with the PTCA surgery.

In one clinical study, when patients were administered Tranilast in a daily oral dose of 600 mg for three consecutive months after PTCA surgery, the incidence of restenosis was less than about 20%.

The incidence of restenosis associated with PTCA surgery usually is about 40%, as reported in Percutaneous Transluminal Coronary Angioplasty, page 179 (1990). Thus, the present invention demonstrates that Tranilast dosage of patients after PTCA surgery is effective for reducing the incidence of restenosis during the treatment period. In patients in which the incidence of restenosis occurs when under Tranilast treatment, the mean degree of stenosis is minimized. The need for a second PTCA intervention is significantly reduced.

When Tranilast or a pharmaceutically acceptable salt thereof is employed therapeutically, it can be administered orally or parenterally in appropriate dosage forms, such as powder, granules, tablets, capsules, injectable solutions, and the like.

A Tranilast pharmaceutical composition can be formulated by admixing suitable carriers such as excipients, disintegrators, binders, brighteners, and the like, and preparing in accordance with conventional molding methods and dosage forms.

For example, a powder dosage form can be formulated by admixing Tranilast or a pharmaceutically acceptable salt thereof with suitable excipients, binders, brighteners, and the like.

Tablets can be formulated by admixing Tranilast or a pharmaceutically acceptable salt thereof with suitable excipients, disintegrators, binders, brighteners, and the like, and compressing the mixture with conventional molding equipment. The tablets also can be coated to provide film-coated tablets, sugar-coated tablets, enteric-coated tablets, and the like.

Capsules can be formulated by admixing Tranilast or a pharmaceutically acceptable salt thereof with suitable excipients, brighteners, and the like, and filling the mixture in capsules, or by forming granules containing Tranilast or a pharmaceutically acceptable salt thereof with conventional molding equipment, and filling the formed granules in capsules.

When a pharmaceutical composition of the present invention is employed therapeutically, the dosage of Tranilast or a pharmaceutically acceptable salt thereof as an active ingredient can be in a range between about 300–1000 mg. A preferred dosage is between about 300–600 mg per adult patient by oral administration on a daily basis for a treatment period of about 3–6 consecutive months after coronary intervention. The dosage and a term of administration are changed depending upon the weight and age and sex of the patient, the severity of the condition to be treated, and the like.

The present invention is further illustrated in more detail by way of the following Examples.

EXAMPLE I

This Example demonstrates the efficacy of the invention method for treatment of restenosis associated with PTCA surgery.

One hundred forty nine lesions with a partial occlusion, which underwent successful PTCA procedures with smooth dilation, were selected for this study. These lesions were divided into two groups, and both groups did not differ significantly with sex, distribution of coronary artery and ratio of lesions restenosed after PTCA; One group (49 lesions) received Tranilast in a daily dose of 600 mg (hereinafter identified as the R group), and the other group (100 lesions) did not receive Tranilast (hereinafter identified as the C group). In addition, all patients were also given calcium antagonists, nitrites and anti-platelets. These drugs were administered for 3 consecutive months after PTCA, and follow-up coronary angiography was performed in 3 months after PTCA.

The measurements were made in two projections using a direct caliper system, and all measurements (before and immediately after PTCA and at final follow-up) were made in the same projection for more accurate comparison.

Diameter stenosis was calculated as the mean of measurements, and restenosis was defined as a loss of at least 50% of the initial gain in luminal diameter accomplished by dilation.

A. The ratio of female-to-male, distribution of coronary vessel, and the ratio of lesions restenosed after PTCA were as follows:
(1) The ratio of female-to-male
 R group: 18%; C group: 29%
(2) Distribution of coronary vessel
 (R group and C group)
 left anterior descending artery: left circumflex artery: right coronary artery = 1:1:1
(3) The ratio of lesions restenosed after PTCA
 R group: 49.0%; C group: 35.6%
B. The results of examination were as follows.
(1) The change of stenosis diameter
 Pre-PTCA
 R group: 68.4%±12.3%;
 C group: 71.1%±11.5%, ns
 Post-PTCA
 R group: 14.8%±11.6%;
 C group: 18.5%±11.0%, ns
 There months after PTCA
 R group: 25.8%±18.2%;
 C group: 41.2%±26.8%, (p<0.001)
(2) The incidence of restenosis
 R group: 12.2%; C group: 38.0% (p <0.01)

The comparative clinical data demonstrate the efficacy of 3 month Tranilast treatment for the prevention of restenosis in patients after PTCA surgery. The following comparative Example demonstrates that a one month Tranilast treatment is not effective for reducing restenosis in patients after PTCA surgery.

EXAMPLE II

This Example illustrates a one month treatment of patients with Tranilast which is not effective for reducing the incidence of restenosis associated with PTCA surgery.

Three hundred fifty two lesions with a partial occlusion, which underwent successful PTCA procedures with smooth dilation, were selected for this study. These lesions were divided into two groups, and both groups did not differ significantly with sex, age, number of diseased vessels, distribution of coronary artery and mean degree of stenosis (%) before PTCA; One group (100 lesions) received Tranilast in a daily dose of 300 mg for 30 consecutive months (hereinafter identified as the R' group), and the other group (252 lesions) did not receive Tranilast (hereinafter identified as the C' group). In addition, all patients were also given calcium antagonists, vasodilators and anti-platelets for 3 consecutive months after PTCA. Follow-up coronary angiography was performed in 3 months after PTCA.

The measurements were made in two projections using a direct caliper system, and all measurements (before and immediately after PTCA and at final follow-up) were made in the same projection for more accurate comparison.

Diameter stenosis was calculated as the mean of measurements, and restenosis was defined as a loss of at least 50% of the initial gain in luminal diameter accomplished by dilation.

The results were as follows:
(1) The change of stenosis diameter
 Pre-PTCA
 R' group: 86.1%; C' group: 78.7%, ns
 Post-PTCA
 R' group: 78.4%; C' group: 22.5%, ns
 Three month after PTCA
 R' group: 78.4%; C' group: 74.9%, ns
(2) The incidence of restenosis
 R' group: 32.1%; C' group: 36.1%, ns The one month treatment with a 300 mg dosage did not have a significant effect in reducing the incidence of restenosis in patients after PTCA surgery.

What is claimed is:

1. A method for the inhibition restenosis associated with coronary intervention in a human patient, which comprises administering to the patient 2-(3,4-dimethoxycinnamoyl)aminobenzoic acid or a pharmaceutically acceptable salt thereof in a daily dose of about 300–1000 mg for a treatment period of at least three consecutive months after coronary intervention.

2. A method in accordance with claim 1 wherein the dosage is between about 300–600 mg of 2-(3,4-dimethoxycinnamoyl)aminobenzoic acid or a pharmaceutically acceptable salt thereof.

3. A method in accordance with claim 1 wherein the treatment period is between about 3–6 consecutive months after coronary intervention.

4. A method in accordance with claim 1 wherein the dosage is administered orally.

5. A method in accordance with claim 1 wherein the dosage is administered parenterally.

6. A method in accordance with claim 1 wherein the coronary intervention is Percutaneous Transluminal Coronary Angioplasty.

7. A method in accordance with claim 1 wherein the coronary intervention is Direction Coronary Atherectomy.

8. A method in accordance with claim 1 wherein the coronary intervention is Stent.

* * * * *

UNITED STATES PATENT AND TRADEMARK OFFICE
CERTIFICATE OF CORRECTION

PATENT NO. : 5,385,935
DATED : January 31, 1995
INVENTOR(S) : Tamai, Ueda, Hsu

It is certified that error appears in the above-indentified patent and that said Letters Patent is hereby corrected as shown below:

Col. 1, line 38, after "an atherectomy catheter" insert a comma.

Col. 4, line 44, "A method for the inhibition restenosis" should be --A method for the inhibition of restenosis--.

Signed and Sealed this

Fifteenth Day of August, 1995

Attest:

BRUCE LEHMAN

*Attesting Officer*   *Commissioner of Patents and Trademarks*